March 20, 1945. B. A. BOURNE Plant Pat. 655
VARIETY OF SUGAR CANE
Filed April 16, 1943 2 Sheets-Sheet 1
FIG. I
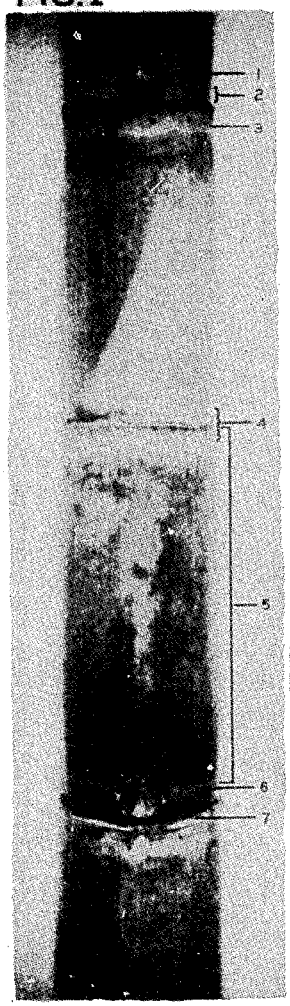
FIG. II
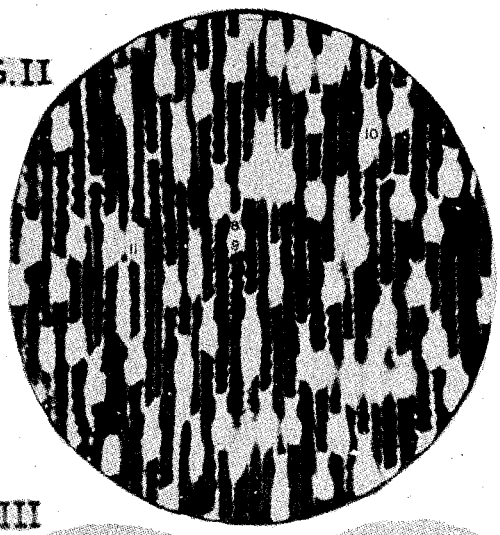
FIG. III
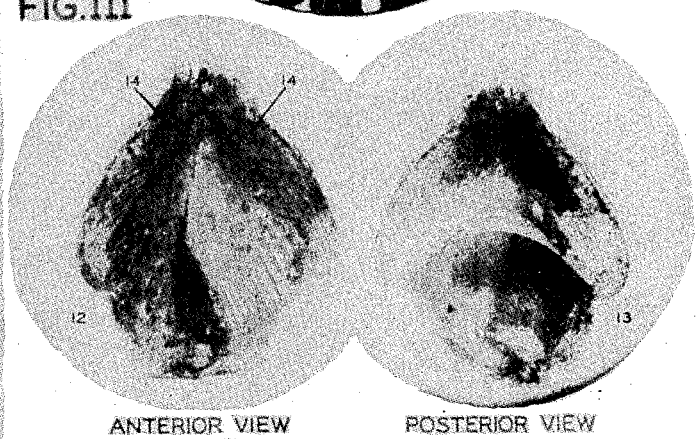
ANTERIOR VIEW POSTERIOR VIEW
FIG. IV
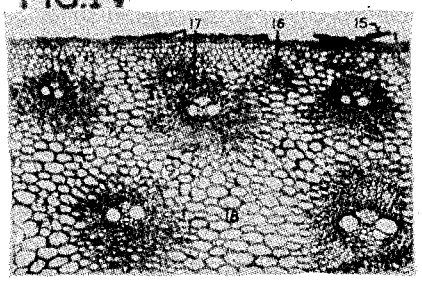
FIG. V
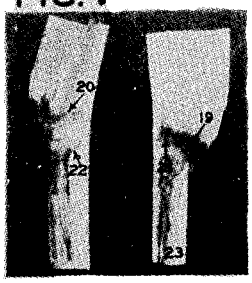
INVENTOR.
Benjamin A. Bourne
BY
Darby & Darby.
Att'ys.

March 20, 1945. B. A. BOURNE Plant Pat. 655
VARIETY OF SUGAR CANE
Filed April 16, 1943 2 Sheets-Sheet 2
FIG. VI
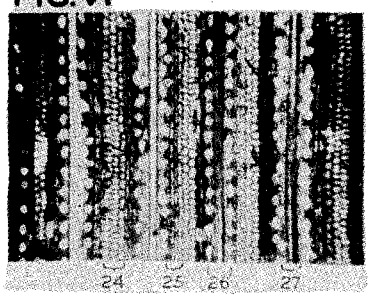
FIG. VII
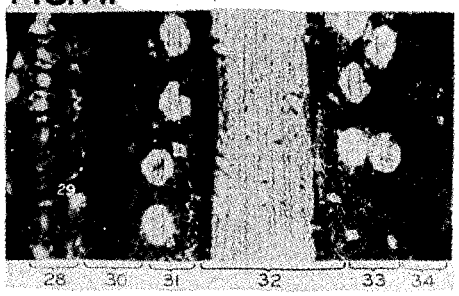
FIG. VIII
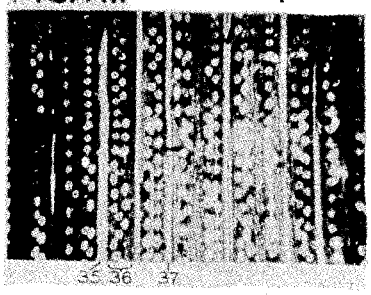
FIG. IX
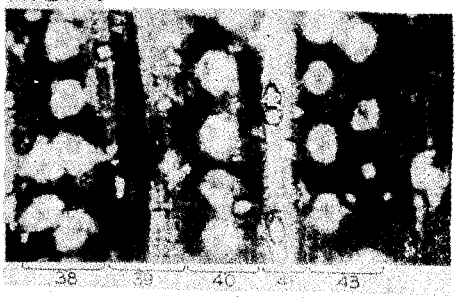
FIG. X
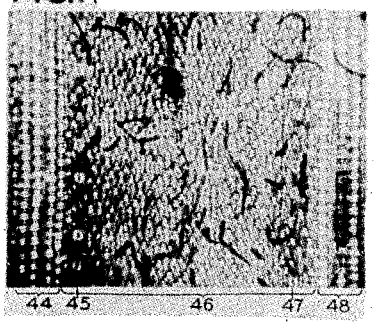
FIG. XI
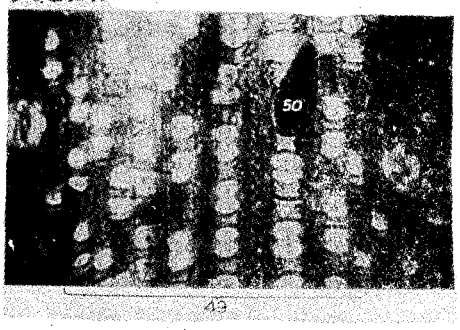
INVENTOR.
Benjamin A. Bourne
by Darby & Darby
Att'ys.

Patented Mar. 20, 1945

Plant Pat. 655

UNITED STATES PATENT OFFICE

655

VARIETY OF SUGAR CANE

Benjamin Arthur Bourne, Clewiston, Fla., assignor to United States Sugar Corporation, Clewiston, Fla., a corporation of Delaware Application April 16, 1943, Serial No. 483,237

1 Claim. (Cl. 47—59)

My new variety originated as a seedling and is the result of a definite breeding effort carried on by me. The crossing of the immediate ancestors of this variety was done by me in December 1935 at Clewiston, Florida. This cross was between two unnamed but numbered seedlings, one of which was in turn originated by me through a cross made several years earlier. The parentage is identical with the commercial variety commonly referred to in original records as F. 31–436 (Plant Patent No. 220) by me in "Facts About Sugar," 34 (8):21–27, illus. 1939, and goes back through several intervening generations to Louisiana Purple and D.74, very well known commercial varieties of *Saccharum officinarum*, to *Saccharum spontaneum* and the variety Chunnee of *Saccharum barberi*, previously used by Jan Kobus for breeding work in Java.

This variety has stalks large in diameter and usually solid in cross section. It is medium to late in maturity. It germinates very well and produces a large number of primary shoots shortly thereafter, thus effecting savings in replanting and early cultivation costs. Although it occasionally produces "suckers" late in the season, the proportion of these is so low that the average quality of the cane is only very slightly effected thereby. On account of the large stalk diameter, solidity and weight it can be hand harvested along with those canes requiring the cheapest rate per ton.

When planted during the fall in the organic soils of the Florida Everglades containing medium to high mineral content, it will, by the first of December of the following year, give sucrose yields amounting to from six to seven per cent by weight of the cane. However, if not harvested as early as December, or slightly more than one year from the date of fall planting it will steadily increase in sucrose content for four to five months, reaching a maximum of nine to thirteen per cent sugar (by weight of cane) depending on the fertility of the soil, weather conditions and suitable fertilization.

Results of comparative trials for five years on organic and sandy soils in Florida show this variety to be very resistant to leaf diseases due to Helminthosporium, very resistant to red rot of the stalk due to *Colletotrichum falcatum* and immune to mosaic disease strains 1 and 4 under natural conditions of field infection in the Florida Everglades. It has an especially strong root system and does not uproot readily under severe weather conditions involving windstorms.

When harvested from late December onwards until late spring it has shown excellent ratooning qualities in spite of several winter frosts. Ratoon growth is rapid in the spring, thus effecting economy in cultivation costs.

The tonnage production of millable cane by comparative tests on the organic soils of the Florida Everglades ranks very high, especially if harvested during February and March. Yields of more than sixty tons per acre as plant cane have been secured frequently, the highest returns being from well-drained, high-mineral muck land in frost-free locations. It is of special promise for use as a rotation variety with existing high cane tonnage commercial canes of the medium to late maturing types on medium to high-mineral organic soils.

The original illustration shows: Figure I, approximate mid-section of typical stalk showing the shape and general appearance thereof. Figure II, typical structure of stem epidermis magnified 295 times. Figure III, anterior and posterior views of a typical stem bud. Figure IV, typical structure of peripheral region of the stem. Figure V, showing typical ligule, auricle and dewlap. Figures VI and VII, typical microscopic appearance of structure of upper epidermis of leaf blade. Figures VIII and IX, typical microscopic appearance of structure of lower epidermis of leaf blade. Figures X and XI, typical microscopic appearance of structure of epidermis of leaf sheath.

The following is a detailed description of my new variety of sugar cane:

*The stalk*

*Structure.*—Stalks are usually solid in cross section and hard. Compared with other sugar canes, they are medium in fiber content, averaging about 10.5 per cent.

*Growth.*—Stalks are semi-erect at first and either remain in that position or may become recumbent later in the growth cycles as their weight increases. Depending on mineral content of organic soil or organic content of sandy soil, weather conditions, fertilization and period of growth, they may attain a length of 6 to 10 feet, or more.

*Size.*—Diameter of stalk as measured from the middles of 20 stalks selected at random (on high-mineral organic soil), varied from 2.2 centimeters to 4.5 centimeters, averaging 3.4 centimeters.

*Internodes.*—Figure I—5—Toward the middle of stalk, internodes may reach a length of 16 centimeters, but were found to vary from 10.0 centimeters to 19.0 centimeters and to average 13.3 centimeters from ten random sample stalk measurements. They usually follow one another in a straight line, but are sometimes slightly "staggered." Location of maximum diameter often occurs above growth ring near base of internode. General bloom is present in considerable amount, is distributed generally over entire surface and is greyish white in color.

*Nodes.*—Somewhat constricted, especially in the vicinity of the wax rings when compared with the middle of the internodal portion. (Figure I—4).

*Color.*—Yellowish green to green at base, but becoming greenish brown to brown or light purple to reddish purple and green toward upper third and top. Typical colors and markings on approximate mid-stalk portions are shown in Figure I. Internal appearance in cross section shows the periphery light green and central portion creamy white.

*Furrows (or eye grooves immediately above the eyes).*—Usually absent in basal and middle portions of stalk but may occur to slight extent toward the top.

*Wax or "Bloom."*—A rather marked bloom present on surface of stem and this is frequently accompanied by a growth or incrustation of "sooty mold" (Figure IV—15) giving the surface a blackish or dirty appearance. The "wax ring" is plainly present below the node (Figure I—3), is broad, heavily coated with wax, constricted slightly and the base line is not distinct, but merges with the general bloom.

*Root band.*—Color is brownish green or green; shape is oblique. Width varies from 0.4 to 0.7 centimeters (Figure I—2), the narrowest width being at side opposite bud.

*Root primordia.*—Number of rows either two or three, irregular and semi-crowded.

*Individual root buds.*—Color in center faintly purplish, with surrounding border pale yellow. Shape round. Contour swollen. Size large and mostly dormant.

*Growth ring.*—Color yellow to yellowish green. Elevated in shape and irregular (Figure I—6). Long cells straight, width 10.36 microns on average from 10 random measurements.

*Rind.*—Splitting or cracking of the rind almost never occurs.

*Leaf scar.*—Prominent (Figure I—7).

*Surface markings.*—Corky cracks sometimes present, especially at the top of the internodes.

*Leaves*

*Number.*—Numerous; average number green leaves per stalk, approximately eight.

*Blade.*—Medium to dark green in color; not striped or variegated; width 5.0 to 7.5 centimeters across widest portions of mature outer blades, averaging 6.5 centimeters from 10 random measurements. Average length from ten random measurements 147.32 centimeters. Ratio of length to width is 22.66:1. Texture smooth. Thick. Veins fairly prominent. Pubescence of leaf edge shows hair group No. 53 present. Color of upper surface of midrib white and of lower surface dark green with light green stripe near center. Cross section of midrib massive. Growth habit is semi-erect with tops bent over or overhanging.

*Structure of upper epidermis.*—The general structure is shown in Figure VI which illustrates typical appearance of the bulbiform band (Figure VI—24), marginal band (Figure VI—25), stomate zones (Figure VI—26) and central zone (Figure VI—27) and their variation and relationship to one another.

*Bulbiform band.*—As illustrated in Figure VI, it varies between two (2) and three (3) cell rows in width. The cell type (Figure VII—28) is honeycomb. Hair group No. 67 is absent.

*Marginal band.*—This is illustrated further in Figure VII—30 and shows it to consist of three cell rows. Two-celled hairs are present (Figure VII—29), as well as spines.

*Stomate zone.*—As illustrated in Figures VI—26 and VII—31, 33, there is usually one row which is frequently staggered. However, occasionally (Figure VII—33) two rows are present.

*Central zone.*—This is illustrated in Figure VII—32 in a typical case. The number of cell rows vary from six to nine. It consists of long cells alternating with short groups. Silica cells rarely present. No spines or hairs seen in this zone. No strand of short cells present in middle of zone.

*Structure of lower epidermis.*—Figure VIII shows the general structure and appearance and illustrates typical intercostal areas with their rows of stomata (Figure VIII—46) and the vein areas (Figure VIII—35, 37).

*Intercostal area.*—As illustrated in Figure VIII the width varies between four and five cell rows. Rows of stomates are variable and may be from one to three. Two-celled hairs in cells bordering stomatal band are occasionally present, but spines are absent.

*Vein areas.*—This is shown also in Figure IX—39, 41 and usually consists of four rows of cells. Spines (Figure IX—42) are fairly abundant and occur in rows.

*Stomatal grooves.*—Absent.

*Blade joint.*—Use is made herein of J. Jeswiet's hair group numbers of Ernst Artschwager's modifications thereof for reference both to certain parts of this portion and to the ligule. The inner surface of the dewlap (or "throat") Figure V—19 represented by hair group No. 52, is coated with short, straight and much appressed hairs over the entire surface in a uniform feltlike covering. Hair group No. 51 is present mainly as an outer marginal band and frequently forms a conspicuous tuft. No band or tuft of long hairs has been observed to be present, such as hair group 58*a*. Hair group 51*a* on inner surface of dewlap is present.

The back or outer surface of the dewlap, or "collar" (Figure V—20) represented by hair group No. 58 is more or less triangular in shape and the surface is covered with a dense feltlike covering of uniformly short hairs. No band or tuft of long hairs has been observed to be present. A coating of wax sometimes obscures the pubescence.

*Pubescence of midrib.*—Hair group No. 55 is present. Hair group 63 is not only present but frequently extends up the midrib for a distance of three (3) centimeters.

*Ligule.*—(Figure V—21). Crescent-shaped. Middle part overlying midrib frequently extends 4 millimeters. The dorsal hairs represented by Jeswiet group No. 66 are dense and cover the surface uniformly. The latter as well as hair group No. 61 usually do not extend more than 1 millimeter above the free margin in the central part of the ligule and are somewhat less prominent above the margin at the flanges. The flanges terminate at the edge of the leaf.

*Leaf sheath.*—(Figure V—23.) Young sheaths approximately 24 centimeters long frequently have a rather hairy patch 12.5 centimeters long commencing 6.3 centimeters from base. The width of such a patch usually is 6 millimeters at base and approximately 2.5 centimeters at top. Spines are 2.5 to 3.0 millimeters long and are frequently persistent, even on old dead sheaths. Outer surface pale yellow green and moderately waxy; base usually straight; overlying margin neither decurrent nor appendaged, thus hair groups 64 and 62 are absent.

*Sheath scar.*—Apparently oblique in many instances although occasionally straight; protruding slightly under bud.

*Sheath joint.*—Frequently oblique and rarely slightly saccate; color of outer surface pale yellow green and that of inner surface purple.

*Sheath pubescence.*—Lateral patch (hair group 60), and marginal fringe (hair group 56), both absent. Also, the peripheral fringe (hair group 59), the dorsal tuft opposite bud (hair group 69) and small black hairs extending into upper region of wax ring were all absent.

*Structure of sheath epidermis.*—The general microscopic appearance of the epidermis is shown in Figure X.

*Intercostal area.*—Figure X—46 shows the typical cell pattern and numerous two-celled hairs present. Large spines are absent. There are two (2) rows of stomates (Figure X—45, 47) each row being situated close to the vein areas (Figure X—44, 48) and are somewhat staggered.

*Vein area.*—Figure XI—49 shows the cell patterns to consist almost entirely of short cells. Spines, Figure XI—50, are present, occur sparsely and are scattered.

*Auricle.*—Outer auricle not developed but inner one calcariform in shape (Figure V—22).

*Leaf stripping.*—The dead leaves and leaf sheaths usually fall away from the stalk at maturity very readily, thus assisting rapid hand harvesting operations without burning.

*Stem buds*

*Size.*—Good, ranging from 1.1 to 1.3 centimeters wide by 1.1 to 1.3 centimeters long.

*Position.*—Not prominent, that is, they do not protrude much from the surface of the stalk. Thus in handling cuttings for planting purposes little bud damage is likely to occur. The tip of the bud protrudes above the growth ring (Figure I—1) and the base is situated at the base of the leaf sheath.

*Form.*—Ovate in shape. Wings (Figure III—14) usually broad and uniform in width and originating below the middle of the anterior side of the prophyllum, or outermost bud scale (Figure III—12). Wing surface not wrinkled, edge entire, tip somewhat truncate and with margin notched but sometimes round pointed. The posterior side of the prophyllum (Figure III—13) is usually heavily coated with a waxy layer which masks the hair groups. For typical form and hair groups, see Figure III showing both anterior and posterior views. Hair groups 8, 11 and 16 are shown in Figure III—12 and hair group 10 in Figure III—13.

*Color.*—Young bud scales green and often turning straw colored when old. Wings of young buds brownish and becoming straw colored with age.

*Membranaceous margin.*—Hair group No. 24 on bud scale absent. Both basal and lateral appendages absent.

*Venation.*—Veins sometimes converging at apex, but old buds commonly exhibit radial venation.

*Germ pore.*—Sub-apical.

*Stem epidermal cells*

The average width of epidermal cells is approximately 10.1 microns, which places the variety in a group of canes having what is considered medium-wide epidermal cells. The number of short-cell groups, (Figure II—8 and 9) per square millimeter is approximately 670. Stomata are rarely present in a microscopic field of 1.9 square millimeters. Pointed, elongated cork cells (Figure II—10) are fairly common. Solitary cork cells are abundant (Figure II—11). Solitary silica cells (Figure II—8) are occasionally present. Epidermal hairs absent.

*Stem peripheral ring*

Typical bundle density within the peripheral ring and relative sizes of these bundles are illustrated in Figure IV. It is seen that small bundles alternate with larger ones (Figure IV—16 and 17), and for the most part large bundles are well separated. The parenchyma surrounding the peripheral bundles (Figure IV—18) are thick-walled and lignified.

*Inflorescence*

This variety occasionally blooms sparsely in the Florida Everglades somewhat late in the season (February or March), but many tassels fail to emerge fully or normally.

The principal characteristics which, in combination, help to distinguish my new variety from all other known varieties of sugar cane, are:

1. Medium to late maturity.
2. Different color and shape of (*a*) stalk and (*b*) bud.
3. Different pattern of stem epidermis.
4. Color, shape, contour, size and dormancy of individual root buds.
5. Characteristic shape and width of cells of growth ring.
6. Different density and relative size of bundles in stem peripheral ring.
7. Different shape and hair characteristics of ligule and dewlap of blade joint.
8. Different shape of inner auricle.
9. Semi-erect growth habit of leaves and stalks, the latter becoming recumbent late in growth cycle. Leaves medium to dark green in color.
10. Characteristic ratio of leaf length to width.
11. Characteristic presence of hair groups described by Jeswiet and Artschwager under 8, 10, 11 and 16 on bud scale and under 51, 51*a*, 52, 53, 55, 58, 61, 63 and 66 on leaf, leaf sheath, blade joint, dewlap and midrib.
12. Characteristic absence of hair groups described by Jeswiet and Artschwager under 24, 58*a*, 59, 62, 64, 67 and 69 on leaf, leaf sheath, blade joint and bud scale.
13. Characteristic microscopic appearance of upper epidermis of leaf blade, including the bulbiform bands, stomatal bands, marginal bands and central zones.
14. Characteristic microscopic appearance of the lower epidermis of leaf blade, including the intercostal and vein areas.

15. Characteristic microscopic appearance of the leaf sheath epidermis, including the intercostal and vein areas.
16. High tonnage and sugar producing ability per acre on the high and medium-mineral organic soils of the Florida Everglades.
17. Marked resistance to certain Helminthosporium fungus leaf diseases common to sugar cane and also to red rot of the stalk. Immune to mosaic disease strains 1 and 4 under natural conditions of field infection in the Florida Everglades.
18. Strength of root system.
19. Resistance to splitting of stalk rind.
20. Very large size and predominantly solid stalks.
21. Good sized buds well protected by their flatness and position.
22. Good germination of cuttings and an early stooler.
23. Good ratooning quality, even after damaging frosts. Rapid ratoon growth in spring.
24. Blooms sparsely or not at all late in the season.
25. Medium in fiber content of stalks.

Having thus disclosed my invention what I claim as new is:

The variety of sugar cane herein shown and described, characterized particularly by its resistance and immunity to certain diseases, high tonnage of cane, good ratooning power, medium to lateness of maturity, distinctive shape of stalk and bud, distinctive pattern of stem epidermis, relative bundle size, bundle density, thickening and lignification of intra-bundle parenchyma of stem peripheral ring, shapes and hair group characteristics of ligule and dewlap, shape of inner auricle, very large and mainly solid stalks.

BENJAMIN ARTHUR BOURNE.